US00PP16489P3

(12) United States Plant Patent
Chahbandar

(10) Patent No.: US PP16,489 P3
(45) Date of Patent: May 2, 2006

(54) ARTICHOKE PLANT NAMED 'BCP 20-18'

(50) Latin Name: ***Cynara scolymus* L.**
Varietal Denomination: BCP 20-18

(76) Inventor: Medhat Chahbandar, Domaine La Quintane, Torreilles (FR), 66440

( * ) Notice: Subject to any disclaimer, the term of this patent is extended or adjusted under 35 U.S.C. 154(b) by 0 days.

(21) Appl. No.: 10/371,882

(22) Filed: Feb. 20, 2003

(65) Prior Publication Data

US 2004/0168241 P1 Aug. 26, 2004

(51) Int. Cl.
*A01H 5/00* (2006.01)

(52) U.S. Cl. ..... Plt./258

(58) Field of Classification Search ..... Plt./258
See application file for complete search history.

(56) References Cited

U.S. PATENT DOCUMENTS

PP14,578 P2 * 3/2004 Colfer ..... Plt./258

* cited by examiner

*Primary Examiner*—Kent L. Bell
*Assistant Examiner*—W. C. Haas
(74) *Attorney, Agent, or Firm*—Townsend and Townsend and Crew LLP

(57) ABSTRACT

A new and distinct cultivar of Artichoke plant named 'BCP 20-18'. This new variety is characterized by a compact shape, a thicker heart, and it matures significantly earlier than other varieties. It has more green (less yellow) overall coloration.

4 Drawing Sheets

Botanical designation: *Cynara scolymus* L.
Variety denomination: 'BCP 20-18'.

BACKGROUND OF THE INVENTION

The present invention comprises a new and distinct cultivar of artichoke plant, botanically known as *Cynara scolymus* L., herein referred to by the cultivar name 'BCP 20-18'. This new variety is characterized by a compact shape that is a little pyramidal in the center, a thick heart, and a darker and more uniform green color (specifically, showing less yellow coloration than the parents). It matures significantly earlier than the parent varieties.

*Cynara scolymus* L., commonly known as Globe artichoke, is a perennial herb and is a member of the family e Asteraceae, also known as the Compositae family. Globe artichokes comprise: leaves, which are pinnately lobed, but primarily spineless; globose capitula composed of overlapping layers of large involucral bracts; and receptacles, which are enlarged and fleshy. Globe artichoke plants are essentially grown for the production of the immature flower heads (or buds). The immature buds are harvested before the appearance of sexual organs (or the mature flower) and are considered vegetable delicacies. Fresh artichokes may be steamed, boiled, or baked after which the fleshy receptacle, inner and outer bracts, and parts of the floral steam may be eaten.

The new cultivar is a product of a planned breeding program carried out by the inventor near Perpignan, France. It originated as a single plant that was selected from a hybrid cross between the artichoke variety 'BCL 9-11' U.S. Plant patent application Ser. No. 10/371,511), the pollen parent; and the artichoke variety 'BH 35-28' (unpatented), the seed parent. The inventor performed asexual reproduction on a single plant of the new cultivar via division. It was demonstrated that the combination of characteristics as herein disclosed for the new cultivar are firmly fixed and retained through successive generations of asexual reproduction.

BRIEF SUMMARY OF THE INVENTION

The following traits have been repeatedly observed and are determined to be basic characteristics of 'BCP 20-18'. These traits in combination distinguish the Artichoke as a new and distinct cultivar from its parent(s) and other varieties known to the breeder. 'BCP 20-18' has a more compact shape that is a little pyramidal in the center, a thick heart, and a darker and more uniform green color (specifically, showing less yellow coloration than the parents). It matures significantly earlier than the parent varieties.

'BCP 20-18' has not been observed under all possible environmental conditions. The phenotype of the new cultivar may vary with variations in environment such as temperature, humidity, light intensity and day length, without any change in the genotype. The following observations, measurements and values describe the new cultivar as grown in Lompoc, Calif. under conditions that closely approximate those generally used in horticultural practice.

Lompoc is located on California's central coast in Santa Barbara County. Conditions can vary in the summer months. Air temperatures can range between the low 60's to 80's. The relative humidity is generally high. Prevailing winds are northwesterly and rainfall averages 12 inches per year.

In the following description, holding quality was measured by the physical appearance of the head. This includes the head's appearance following 3 and 7 day storage periods in cold storage at 34° F. The head's exterior (oxidation) was observed at each of the two observation points. Browning and blackening of plant tissue was evaluated as light, moderate and extreme. Overall storage response was measured by observing heads following 3 and 7 day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, necrotic or chlorotic lesions or any abiotic responses to environmental conditions.

BRIEF DESCRIPTION OF THE DRAWINGS

This new variety is illustrated by the accompanying photographic drawings. The colors in the photographs are as true to those of the plant as can be reasonably obtained from conventional photographic procedures.

DETAILED DESCRIPTION OF THE INVENTION

Figure 1:
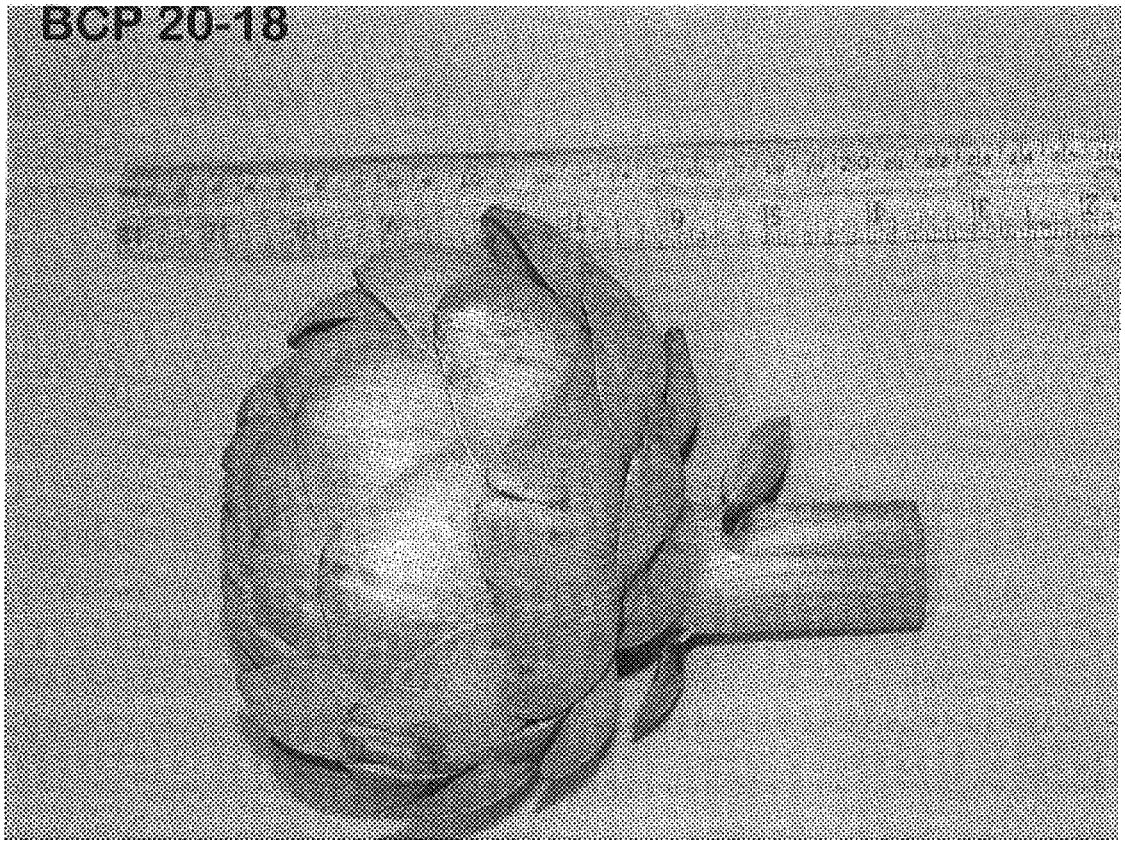
FIG. 1 shows a side elevational view of 'BCP 20-18's fruit in full color.
Figure 2:
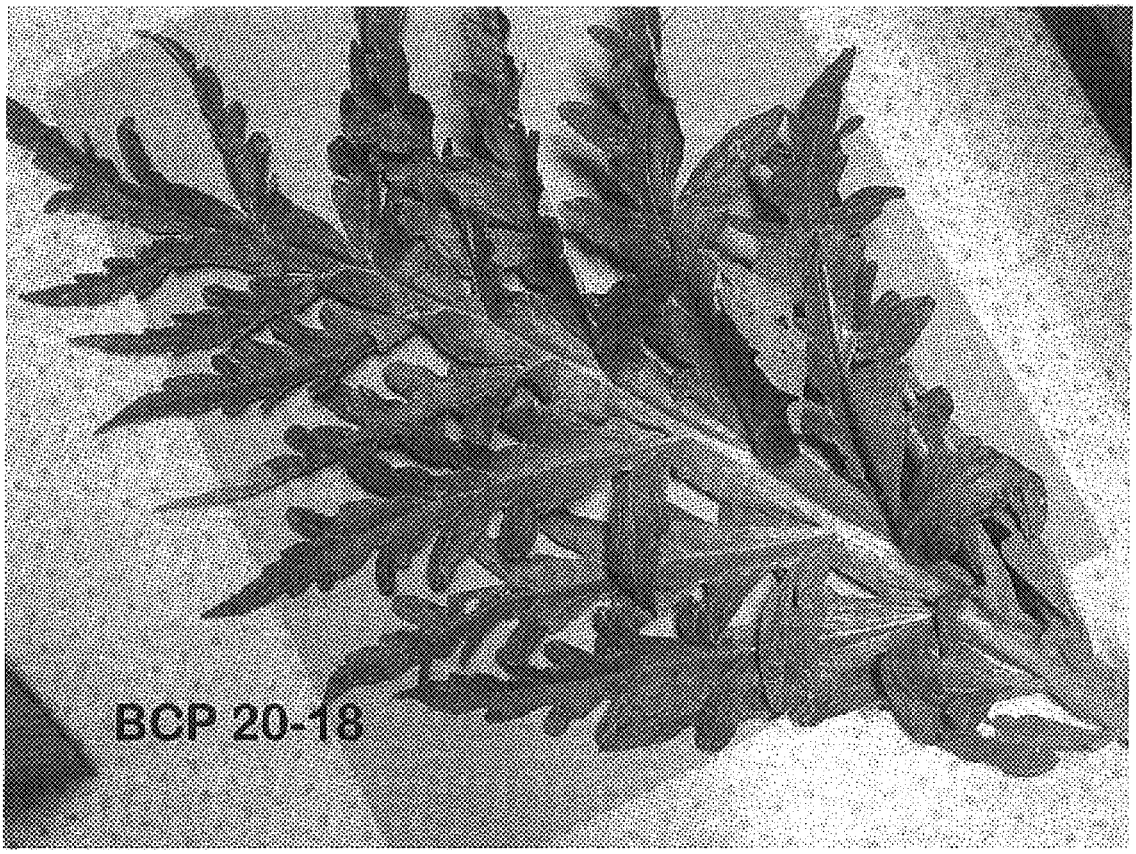
FIG. 2 shows a side elevational view of 'BCP 20-18's foliage in full color.
Figure 3:
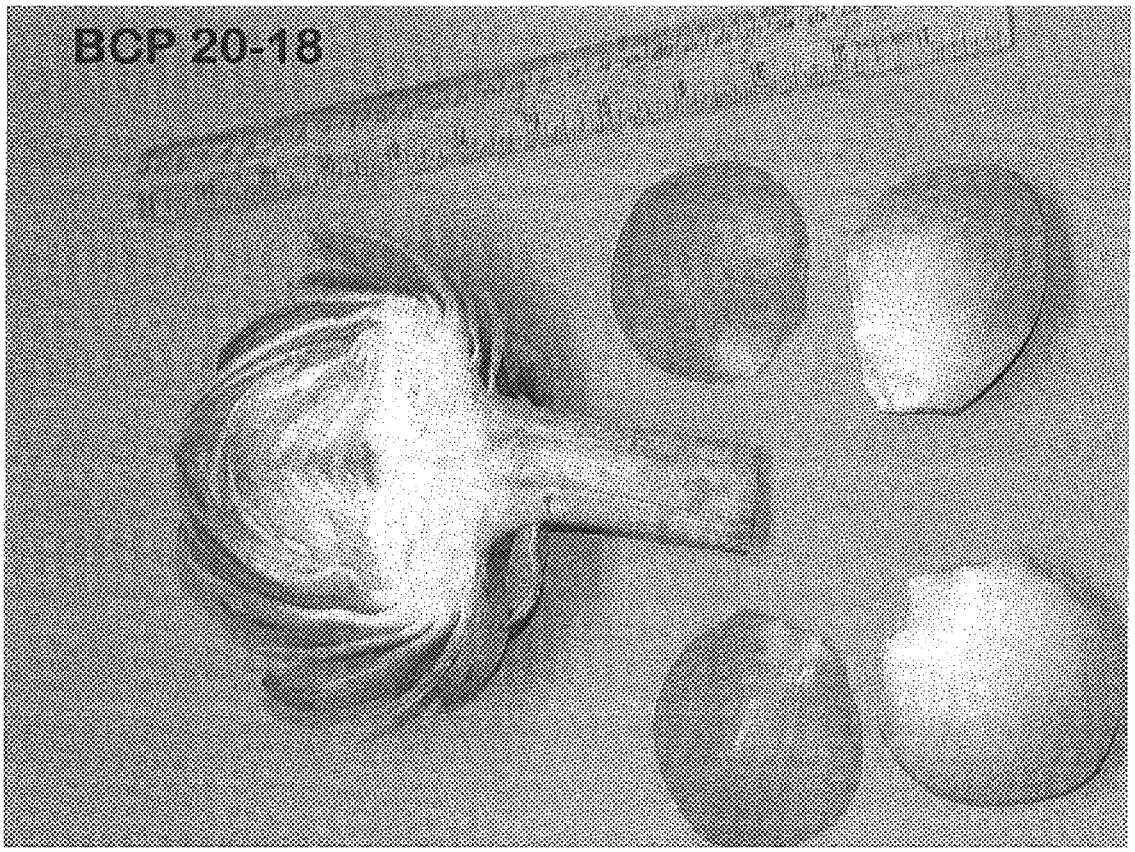
FIG. 3 shows a close-up view of the vertical cross-section of 'BCP 20-18's fruit in full color.
Figure 4:
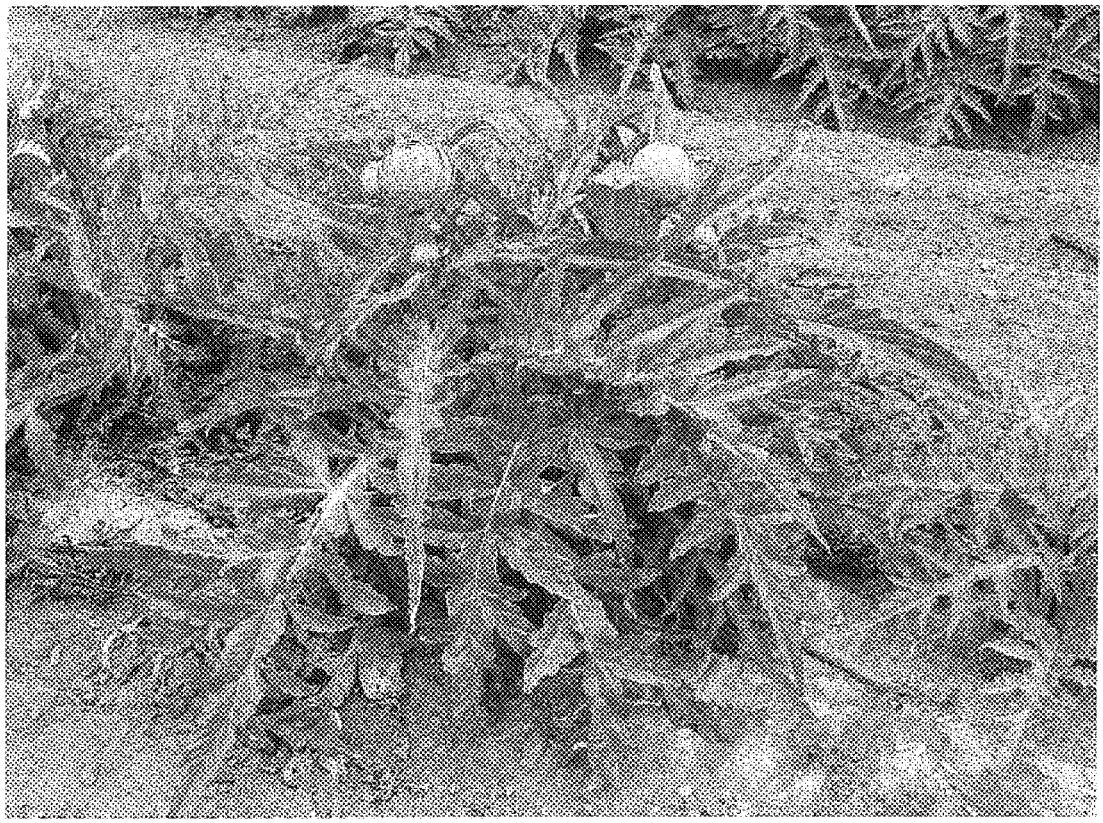
FIG. 4 shows a side elevational view of the 'BCS 20-18' plant in whole.

The following observations, measurements, and values describing the new artichoke plant are based upon observations of plants grown in Lompoc, Calif. The parent cultivars are, to the inventor's knowledge, the closest prior art to the claimed plant variety. The variety was selected as a single plant that was then reproduced. Selection was performed in an outdoor field setting. Unless otherwise indicated, the data were collected from plants that originated from asexually reproduced plants that had been grown in Perpignan by micropropagation, acclimatized in California, and then vegetatively divided. The plants were grown in the soil in rows where row spacing (bed centers) was at 80 inches, and individual plant spacing at 36 inches. Unless otherwise indicated, the measurements described herein were obtained from plants grown in accordance with the following: after acclimatization, plants were planted in the field in July 2001 and harvested in March of 2002. The plants were cut back and split. New plants were planted in July of 2002 and measurements performed in December of 2002 or January of 2003. Color references are measured against The Royal Horticultural Society Colour Chart.

Plant growth is indicated below as "moderate". Exemplary growth data showed that plants planted from tissue culture on Jun. 9, 2004 grew to an average of 55 inches in height and 97 inches in width by Jan. 26, 2005; and plants planted from tissue culture on Jul. 1, 2004 grew to an average of 48.5 inches in height and 101 inches in width by Jan. 26, 2005.

General:

*Parentage.*—Hybrid cross of 'BCL 9-11' (pollen parent) and 'BH 35-28' (seed parent).

*Classification.*—*Cynara Scolymus* L.

*Propagation.*—Asexual production by division.

Plant:

*Height.*—106.7 to 121.9 cm; average 114.3 cm.

*Width.*—205.7 to 238.8 cm; average 226.1 cm.

*Form.*—Full.

*Growth habit.*—Upright, with a partial spread of leaves and shoots.

*Vigor.*—Moderate.

Main stem:

*Main stem diameter.*—6.74 to 11.4 cm; average 8.7 cm.

*Main stem length.*—Approximately 112.4 to 149.2 cm.

*Main stem width* (*w/leaves*).—Approximately 71.1 to 94.0 cm.

*Average internode distance.*—Approximately 6.1 to 8.7 cm.

Side shoots:

*Length.*—12 to 40 cm; mean 32 cm.

*Diameter.*—1.7 to 2.8 cm; means 2.3 cm.

*No. of leaves per shoot.*—2 to 4 leaves.

*Average internode distance.*—5.5 to 7 cm.

*Number per plant.*—Average of 6.8 per plant.

*Development.*—Vigorous.

*Color.*—Green Group between 139C and 139D, highly pubescent.

Capitulum:

*Primary size.*—Approximately 13.3 cm.

*Shape.*—Compact, round, with pyramidal top.

*Texture.*—Hard and smooth.

*Fragrance.*—Mild.

*Average bud weight.*—400 to 550 gm.

*Color.*—Green group 141D.

Bract:

*Length.*—Approximately 7 cm.

*Width.*—Approximately 5.5 cm.

*Shape.*—Predominantly ovate, longer than broad, and thick.

*Texture.*—Hard and smooth.

*Number.*—186 per head.

*Color* (*inner*).—Green group 141D.

*Color* (*outer*).—Green group 141D.

*Firmness.*—Firm and fleshy with thick basal thickness.

*Spinosity.*—None, or minimal —less than 1 mm.

*Basal thickness.*—6 to 17 mm.

Miscellaneous:

*Heart description.*—Concave full, flatter than 'Green Globe' (unpatented), well developed with thick bract connection.

*Receptacle thickness.*—1.6 cm.

*Heart color.*—Yellow green group between 145B and 145C.

*Florets.*—Sterile.

*Pappus length.*—1.4 cm.

*Pappus color.*—Yellow green group 145D.

*Head firmness.*—Firm, heads are dense and solid.

*Gloss.*—Less glossy than 'Green Globe'.

*Cold storage* (*hold quality*).—Good, heads remain firm and free of decay; slight leaf discoloration with cut stem turning brown. Stem was semi-soft after 7 days.

*Head response* (*weather*).—No adverse responses to weather conditions were observed on heads or other plant tissues more sensitive to freezes than similar varieties.

*Disease.*—Older leaves are susceptible to Ramularia_ leaf spot.

*Bud burst.*—March 10 to March 30.

Foliage:

*Leaf shape.*—Long, narrow, slightly oval overall, with multiple lobes such that the outer edges appear coarsely serrated, wherein the apex is acute and petiole attaches to the center of a slightly obcordate bas.

*Foliage density.*—Dense; many large leaves off main stem with leafy side shoots development as well.

*Distance between main lobes.*—Approximately 9.3 to 10.5 cm.

*No. of leaves on main stem.*—8 to 20 leaves.

*Leaf ratio.*—Approximately 1.5 to 1.7 cm.

*Leaf area.*—Approximately 3,147 to 5,521 cm sq.

*Upper leaf surface color.*—Green group between 137A and 137B.

*Lower leaf surface color.*—Green group 136C.

*Texture.*—Lightly but uniformly textured; glossy with rough intervenal texture.

*Pubescence.*—Sparse, some visible pubescence on lower leaf surface.

*Lobe width.*—Approximately 13.3 to 24.8 cm.

*Lobe indentation.*—Approximately 9.5 to 19.7 cm.

*Petiole length.*—Approximately 33.0 to 38.1 cm.

*Petiole width.*—Approximately 3.2 to 7.4 cm.

*Petiole thickness.*—Approximately 2.2 to 3.2 cm.

*Petiole color.*—Green group between 142B and 142C.

*Petiole texture.*—Spindled, wherein multiple ridges, running parallel to the lengthwise orientation, radiate around the petiole.

What is claimed is:

1. The new and distinct variety of artichoke plant substantially as shown and described herein.

* * * * *